(12) United States Patent
Swartz et al.

(10) Patent No.: US 7,977,114 B2
(45) Date of Patent: Jul. 12, 2011

(54) METHOD AND APPARATUS FOR MONITORING PROCESSES USING A SINGLE DETECTOR

(75) Inventors: Michael Swartz, Uxbridge, MA (US); Charles H. Fraiser, Hopkinton, MA (US); Patricia Ann Fowler, Upton, MA (US); Michael D. Jones, Narraganset, RI (US)

(73) Assignee: Waters Technologies Corporation, Milford, MA (US)

( * ) Notice: Subject to any disclaimer, the term of this patent is extended or adjusted under 35 U.S.C. 154(b) by 1466 days.

(21) Appl. No.: 11/240,520

(22) Filed: Sep. 30, 2005

(65) Prior Publication Data

US 2006/0093521 A1 May 4, 2006

Related U.S. Application Data

(63) Continuation of application No. PCT/US2004/010334, filed on Apr. 2, 2004.

(60) Provisional application No. 60/460,598, filed on Apr. 4, 2003.

(51) Int. Cl.
*G01N 30/02* (2006.01)
*G01N 30/38* (2006.01)

(52) U.S. Cl. ...... 436/161; 422/70; 73/61.56; 210/198.2; 210/656

(58) Field of Classification Search .................. 436/161; 422/70, 89; 73/23.36, 23.42, 61.56; 210/198.2, 210/656; 95/82; 96/102
See application file for complete search history.

(56) References Cited

U.S. PATENT DOCUMENTS 5,108,708 A * 4/1992 Hanus .......................... 422/100
6,344,172 B1 * 2/2002 Afeyan et al. .................. 422/70

OTHER PUBLICATIONS http://www.lcresources.com/discus/messages/5133/937.html?FridayMay2620000236pm.*

* cited by examiner

*Primary Examiner* — Jan M Ludlow
(74) *Attorney, Agent, or Firm* — Guerin & Rodriquez, LLP

(57) ABSTRACT

Embodiments of the invention feature methods and apparatus for the efficient utilization of detectors and other components. The apparatus comprises a pump for receiving and propelling one or more samples in a fluid path. The apparatus further comprises a valve element in fluid communication with the pump for receiving the samples from the pump and directing the sample along one fluid path selected from a group. The group comprises a delay path comprising a delay volume, and a chromatography assembly having at least one chromatography column. The apparatus further comprises a detector or grouping of detectors in fluid communication with the delay path and the chromatography assembly for detecting compounds of interest to allow a single detector or single grouping of detectors to receive samples from the two fluid paths.

22 Claims, 1 Drawing Sheet

METHOD AND APPARATUS FOR MONITORING PROCESSES USING A SINGLE DETECTOR

CROSS REFERENCE TO RELATED APPLICATIONS

This application claims benefit of and is a continuation of International Application No. PCT/US2004/010334, filed Apr. 2, 2004 and designating the United States, which claims benefit of a priority to U.S. Provisional Application No. 60/460,598, filed 4 Apr. 2003. The content of which is expressly incorporated herein by reference in its entirety.

FIELD OF THE INVENTION

The present invention related to analytical instruments and techniques.

BACKGROUND OF THE INVENTION

Analytical equipment is expensive. Operating analytical equipment is also expensive requiring highly skilled operators and technicians. In the past it was necessary to perform analyses of certain processes with distinct and separate detectors and other specialized ancillary equipment. These separate and distinct detector and ancillary equipment are an impediment to automation and cost efficient research.

As used herein, the term "detectors" is used to denote apparatus and devices which receive a sample and produce a signal based on the sample composition. By way of example without limitation, detectors comprise mass spectrometers, refractometers, light scattering detectors, fluorescent and chemi-luminescent detectors, conductivity detectors, and other electrochemical or physical chemical detectors. The term "detecting" is used broadly to mean determining the presence, or absence, or concentration of a compound of interest. Sometimes detectors are grouped, plumbed in series or parallel from a single fluid line, to produce multiple signals from a single sample. Such commonly plumbed detectors are referred herein as a detector group.

As used herein, the term "processes" refers to chemical reactions, physical changes, dissolution, affinity and disassociation events and the like.

The term "chromatography" refers to the separation of compounds due to affinity to a medium.

It would be desirable for a single process to be able to be monitored by a single detector to obtain real time data as to the events of the process and to effect analytical data as to the nature of the compounds present.

SUMMARY OF THE INVENTION

The present invention features methods and apparatus for monitoring processes using a single detector or grouping of detectors. One embodiment of the present invention features an apparatus for detecting one or more compounds of interest in one or more samples by liquid chromatography and one or more analyses. The apparatus comprises a pump for receiving and propelling one or more samples in a fluid path. The apparatus further comprises a valve element in fluid communication with the pump for receiving the samples from the pump and directing the sample along one fluid path selected from a group. The group comprises a delay path comprising a delay volume, and a chromatography assembly having at least one chromatography column. The apparatus further comprises a detector or grouping of detectors in fluid communication with the delay path and the chromatography assembly for detecting compounds of interest to allow a single detector or single grouping of detectors to receive samples from the two fluid paths. Thus the invention provides efficient utilization of detectors and other components and is readily subject to automation.

For example, one preferred embodiment of the present apparatus features control means. As used herein, "control means" refers to one or more computers which though hardware, software, embedded software or the like is capable of directing signals to components or receiving signals from components. Signals can be in the form of data and or instructions. Preferably, the control means is constructed and arranged to send one or more signals to the valve element to direct the valve element to direct the sample along one of said fluid paths.

Preferably, the control means is constructed and arranged to receive one or more signals from the detector indicative of the presence of a compound of interest. Thus, the control means can send a signal to the valve element to direct the valve element to direct the sample to one of the fluid paths upon receiving signals indicative of the presence of the compound of interest. For example, in one embodiment the control means directs the valve element to direct the sample to the delay path until the control means receives a signal from the detector of the presence of the compound of interest and, thereafter, to the chromatography assembly.

And, preferably, the control means receives one or more signals indicative of the absence of the compound of interest. Thus, in one embodiment the control means directs the sample to the delay path after receiving a signal of the presence of the compound of interest in the chromatography path and subsequently receiving a signal of its absence.

The control means may also direct the sample to one of said fluid paths periodically.

Preferably, the delay path comprises a knitted reaction coil to reduce bandspreading. The chromatography assembly comprises one or more solid phase extraction devices, or simply, chromatography columns and cartridges, plumbed through suitable fittings and tubing.

Embodiments of the present invention are suited for the study of dissolution events, such as evaluating solid dosage forms, tablets and capsules and the like, for proper dissolution. Preferably, the apparatus further comprises a dissolution assembly, for dissolving one or more solid dosage forms and placing a drug in a solution. The solution with drug forms one or more samples. Dissolution assemblies typically comprise one or more baths and vessels to hold dissolving tablets and capsules. The dissolution assembly preferably comprises one or more transfer modules to transfer a sample to the pump or other equipment in association with the pump.

One typical component of equipment often associated with the pump is an autosampler module. The autosampler module is in communication with the pump for placing samples into fluids received by the pump.

Thus, the present apparatus makes efficient use of detectors. Where the cost of detectors, such as ultra violet light detectors, refractometers, mass spectrometers, fluorescent and chemi-luminescent detectors, light scattering detectors, electro-chemical detectors, conductivity detectors, may be substantial, the present invention offers great benefits.

A further embodiment of the present invention features a method of monitoring a process for the presence, absence or concentration of a compound of interest. The method comprising the steps of providing an apparatus as previously described; and, directing a sample into the pump, to propel the sample to at least one of the fluid paths and monitoring the detector for the presence or absence or concentration of the compound of interest.

Preferably, the method is automated with control means constructed and arranged to send one or more signals to the valve element to direct the valve element to direct the sample along one of the fluid paths. And, preferably, the control means is constructed and arranged to receive one or more signals from the detector indicative of the presence of a compound of interest. Thus, the control means preferably and automatically sends a signal to the valve element to direct the valve element to direct the sample to one of the fluid paths upon receiving signals indicative of the presence of the compound of interest.

For example, the control means preferably directs the valve element to direct the sample to the delay path until the control means receives a signal from the detector of the presence of the compound of interest and thereafter directs the sample to the chromatography assembly. Preferably, the control means receives one or more signals indicative of the absence of the compound of interest. And, the control means directs the sample to the delay path after receiving a signal of the presence of the compound of interest in the chromatography path and subsequently receiving a signal of its absence.

In the alternative, the method may require the control means to direct the sample to one of said fluid paths periodically.

These and other advantages and features of the present invention will now be described with respect to the figures and detailed description that follow.

DETAILED DESCRIPTION OF THE DRAWINGS

Figure 1:
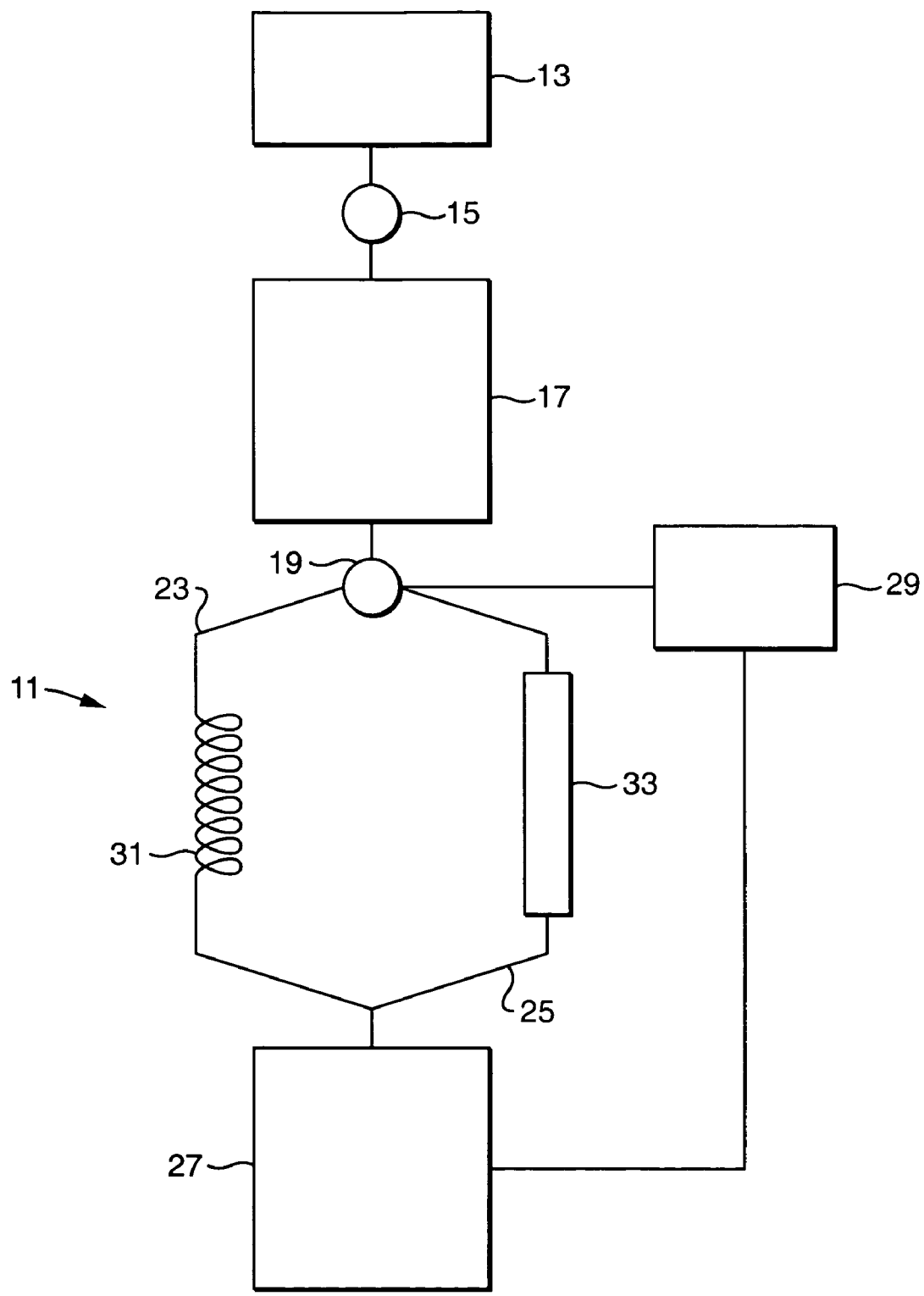
FIG. 1 depicts a schematic diagram of an apparatus embodying features of the present invention.

The present invention will be described with respect apparatus and methods for performing solid dosage form dissolution studies. However, those skilled in the art will recognize that embodiments of the present invention have applications for monitoring many reactions and processes.

Turning now to FIG. 1, an apparatus, generally designated by the numeral 11, is depicted which apparatus embodies features of the present invention. Apparatus 11 is for detecting one or more compounds of interest in one or more samples by liquid chromatography and one or more analyses. Apparatus 11 has the following major elements, a dissolution system 13, a sample transfer module 15, a pump 17, a valve 19, a delay volume path 23, a chromatograph assembly 25, one or more detectors 27 (only one shown) and control means in the form of a computer 29.

Dissolution assembly 13 receives solid dosage forms such as tablets, capsules, pills and the like in vessels (not shown). These solid dosage forms in the vessels are immersed in solutions for dissolving. These solutions may mimic the normal stomach conditions. Typically, aliquots of the solutions, as the solid dosage form is being dissolved, are taken and analyzed to determine the extent of drug released. For the purpose of the present discussion, these aliquots are the samples. The compounds of interest will normally comprise one or more of the active ingredients of the solid dosage form. Dissolution assemblies 13 are available from several venders. A preferred dissolution assembly 13 is the Hanson SR8-Plus™ (Chatsworth, Calif., USA).

Transfer module 15 is in fluid communication with the vessels of the dissolution assembly 13 and pump 17. Transfer module 15 receives sample from the dissolution assembly 13 and transfers the sample to the pump 17 or other equipment in association with the pump 17. A preferred transfer module 15 is a transfer module sold as the WATERS Transfer Module (Waters Corporation, Milford, Mass., USA).

One typical component of equipment often associated with the pump 17 is an autosampler module (not shown). The autosampler module is in communication with the pump 17 for placing samples into fluids received by the pump. Pump 17 and autosamplers are sold separately and as a single entity from numerous venders. A preferred pump 17 and autosampler is sold as the WATERS Alliance™ 2695D Separations Module (Waters Corporation, Milford, Mass., USA).

Pump 17 receives samples from dissolution system 13 and sample transfer module 15 and propels such samples in a fluid path. The apparatus 11 further comprises valve element 19 in fluid communication with pump 17 for receiving the samples from pump 17 and directing the sample along one fluid path selected from a group. The group comprises a delay path 23 and a chromatography assembly 25. Valve elements 19 are available from numerous venders. However, a preferred valve element 19 is incorporated in the WATERS Alliance™ 2695D Separations Module (Waters Corporation, Milford, Mass., USA).

The delay path 23 comprises a volume of tubing which delays the sample. A preferred delay path 23 comprises a peak stabilizing device 31 having a knitted coil open tube design. A preferred peak stabilizing device 31 is sold as part number 030805, RXN-1000 Coil by Waters Corporation (Milford, Mass., USA).

A preferred chromatography assembly comprises tubing and one or more chromatography columns or cartridges, of which only one is shown, designated 33. Chromatography columns and cartridges are available from numerous venders.

The apparatus 11 further comprises detector 27 in fluid communication with the delay path 23 and the chromatography assembly 25 for detecting compounds of interest. Although only one detector 27 is depicted, a group of detectors can be used to allow a single detector or single grouping of detectors to receive samples from the two fluid paths 23 and 25. A preferred detector 27 comprises a dual wavelength absorbance detector sold by Waters Corporation (Milford, Mass., USA) under the trademark 2487™. However, detector 27 may comprise any ultra violet light detector, refractometer, mass spectrometer, fluorescent and chemi-luminescent detector, light scattering detector, electro-chemical detector. More than one detector may be plumbed in series or in parallel to detector 27 to provide additional information.

The invention provides efficient utilization of detectors and other components and is readily subject to automation. Apparatus features control means in the form of computer 29. Computers such as computer 29 are available from numerous venders. Computer 29, through hardware, software, embedded software or the like is capable of directing signals to components or receiving signals from components. Signals can be in the form of data and or instructions. A preferred software to operate the computer 29 is instrument control and data management software product sold by Waters Corporation (Milford, Mass., USA) under the trademark EMPOWER™. Computer 29 is constructed and arranged to send one or more signals to the valve element 19 to direct the valve element 19 to direct the sample along one of said fluid paths 23 or 25. Computer 29 may also be constructed and arranged to receive signals and send directions to the pump 17, transfer module 15, and dissolution assembly 13. Lines indicating such communications are not shown for simplification of the drawings. Computer 29 may communicate with valve element 19 through the pump 17.

Preferably, the computer 29 is constructed and arranged to receive one or more signals from the detector 27 indicative of the presence of a compound of interest. Thus, the computer 29 can send a signal to the valve element 19 to direct the valve element 19 to direct the sample to one of the fluid paths 23 or 25 upon receiving signals indicative of the presence of the compound of interest. For example, computer 29 directs the valve element 19 to direct the sample to the delay path 23 until the computer 29 receives a signal from detector 27 of the presence of the compound of interest and, thereafter, to the chromatography assembly 25.

Computer 29 receives one or more signals indicative of the absence of the compound of interest. Thus, computer 29 directs the sample to the delay path 23 after receiving a signal of the presence of the compound of interest in the chromatography path 25 and subsequently receiving a signal of its absence.

The computer 29 may also direct the sample to one of said fluid paths periodically or at the direction of the operator.

The operation of apparatus 11 will be described with respect to a method of monitoring a process for the presence, absence or concentration of a compound of interest in accordance with the present invention. The method comprising the steps of providing an apparatus 11 as previously described; and, directing a sample into the pump 17, to propel the sample to at least one of the fluid paths 23 and 25. The detector 27 is monitored for signals indicative of the presence of absence or concentration of the compound of interest. As used herein the term "monitored" is used in sense of taking readings and analyzing data.

As described, the method is automated with computer 29 constructed and arranged to send one or more signals to the valve element 19 to direct the valve element 19 to direct the sample along one of the fluid paths 23 and 25. And, the computer 29 is constructed and arranged to receive one or more signals from the detector 27 indicative of the presence of a compound of interest. Thus, the computer 29 automatically sends a signal to the valve element 19 to direct the valve element 19 to direct the sample to one of the fluid paths upon receiving signals indicative of the presence of the compound of interest.

The computer 29 preferably directs the valve element 19 to direct the sample to the delay path 23 until the computer 29 receives a signal from detector 27 of the presence of the compound of interest and, thereafter, directs the valve element 19 to send the sample to the chromatography assembly 25. Preferably, the computer 29 receives one or more signals indicative of the absence of the compound of interest. And, the computer 29 directs the sample to the delay path 23 after receiving a signal of the presence of the compound of interest in the chromatography path 25 and subsequently receiving a signal of its absence.

Operators may require the computer 29 to direct the sample to one of the fluid paths 23 or 25 periodically or select one of the paths for a series of studies.

The embodiments of the present invention have been described with respect to the figure and detailed description with the understanding that such description and figure is merely illustrative of the preferred embodiments. The invention is subject to modification and alteration without departing from the teaching herein and all such modifications and alterations shall be part of the invention defined with greater particularity in the claims which follow.

What is claimed is:

1. An apparatus for monitoring processes for the presence or absence of one or more compounds of interest in dissolution samples by liquid chromatography, comprising:
   a. a dissolution assembly for receiving dosage forms capable of dissolution and subjecting such dosage forms to conditions for dissolution during a dissolution period and forming a dissolution fluid which changes concentration of the one or more compounds of interest during said dissolution period;
   b. an autosampler in communication with said dissolution assembly for withdrawing aliquots of said dissolution fluid at different times to form one or more samples corresponding to the degree of dissolution of the dosage form during the dissolution period;
   c. a pump for receiving and propelling one or more samples in a fluid path;
   d. a valve element in fluid communication with said pump for receiving said samples from said pump and directing said sample along one fluid path selected from the group consisting of a first fluid path and a second fluid path;
   e. said first fluid path comprising a delay path comprising a delay volume wherein said delay path comprises a knitted reaction coil to reduce bandspreading;
   f. said second fluid path comprising a chromatography assembly having at least on chromatography column; and
   g. at least one detector in fluid communication with said delay path and said chromatography assembly for detecting the one or more compounds of interest to allow said at least one detector to receive samples from said two fluid paths.

2. The apparatus of claim 1 further comprising control means, said control means constructed and arranged to send one or more signals to said valve element to direct said valve element to direct said sample along one of said fluid paths.

3. The apparatus of claim 2 wherein said control means is constructed and arranged to receive one or more signals from said at least one detector indicative of the presence of said one or more compounds of interest.

4. The apparatus of claim 3 wherein said control means sends a signal to said valve element to direct said valve element to direct said sample to one of said fluid paths upon receiving signals indicative of the presence of said one or more compounds of interest.

5. The apparatus of claim 4 wherein said control means directs said valve element to direct the sample to said delay path until said control means receives said signal from said at least one detector of the presence of the one or more compounds of interest and thereafter to said chromatography assembly.

6. The apparatus of claim 5 wherein said control means receives one or more signal indicative of the absence of the one or more compounds of interest.

7. The apparatus of claim 6 wherein said control means directs said sample to said delay path after receiving a signal of the presence of said one or more compounds of interest in said chromatography path and subsequently receiving a signal of its absence.

8. The apparatus of claim 2 wherein said control means directs said sample to one of said fluid paths periodically.

9. The apparatus of claim 1 wherein said dissolution assembly comprises one or more baths.

10. The apparatus of claim 9 wherein said dissolution assembly comprises one or more transfer modules.

11. The apparatus of claim 1 wherein said at least one detector is selected from the group consisting of ultra violet light detectors, refractometers, mass spectrometers, flourescent and chemi-luminescent detectors, conductivity detectors, light scattering detectors, and electro-chemical detectors.

12. A method for monitoring a process for the presence or absence or concentration of one or more compounds of interest in dissolution samples by liquid chromatography, comprising the steps of:
   a. providing an apparatus comprising:
      i. a dissolution assembly for receiving dosage forms capable of dissolution and subjecting such dosage forms to conditions for dissolution during a dissolution period and forming a dissolution fluid which changes concentration of the one or more compounds of interest during said dissolution period;
      ii. an autosampler in communication with said dissolution assembly for withdrawing aliquots of said dissolution fluid at different times to form one or more samples corresponding to the degree of dissolution of the dosage form during the dissolution period;
      iii. a pump for receiving and propelling one or more samples in a fluid path;
      iv. a valve element in fluid communication with said pump for receiving said samples from said pump and directing said sample along one fluid path selected from the group consisting of a first fluid path and a second fluid path;
      v. said first fluid path comprising a delay path comprising a delay volume wherein said delay path comprises a knitted reaction coil to reduce bandspreading;
      vi. said second fluid path comprising a chromatography assembly having at least one chromatography column;
      vii. at least one detector in fluid communication with said delay path and said chromatography assembly for detecting said one or more compounds of interest to allow said at least one detector to receive samples from said two fluid paths; and
   b. directing a sample into said pump, to propel said sample to at least one of said fluid paths and monitoring said at least one detector for the presence or absence or concentration of said one or more compounds of interest.

13. The method of claim 12 wherein the apparatus further comprising control means, said control means constructed and arranged to send one or more signals to said valve element to direct said valve element to direct said sample along one of said fluid paths.

14. The method of claim 13 wherein said control means is constructed and arranged to receive one or more signals from said at least one detector indicative of the presence of said one or more compounds of interest.

15. The method of claim 14 wherein said control means sends a signal to said valve element to direct said valve element to direct said sample to one of said fluid paths upon receiving signals indicative of the presence of said one or more compounds of interest.

16. The method of claim 15 wherein said control means directs said valve element to direct the sample to said delay path until said control means receives said signal from said at least one detector of the presence of the one or more compounds of interest and thereafter to said chromatography assembly.

17. The method of claim 16 wherein said control means receives one or more signal indicative of the absence of the one or more compounds of interest.

18. The method of claim 17 wherein said control means directs said sample to said delay path after receiving a signal of the presence of said one or more compounds of interest in said chromatography path and subsequently receiving a signal of its absence.

19. The method of claim 13 wherein said control means directs said sample to one of said fluid paths periodically.

20. The method of claim 12 wherein said dissolution assembly comprises one or more baths.

21. The method of claim 12 wherein said dissolution assembly comprises one or more transfer modules.

22. The method of claim 12 wherein said at least one detector is selected from the group consisting of ultra violet light detectors, refractometers, mass spectrometers, florescent and chemi-luminescent detectors, conductivity detectors, light scattering detectors, and electro-chemical detectors.

* * * * *